(12) United States Patent
Ushpizin (10) Patent No.: US 11,707,292 B2
(45) Date of Patent: Jul. 25, 2023

(54) DISC CLEANING SURGICAL TOOL

(71) Applicant: Mazor Robotics Ltd., Caesarea (IL)

(72) Inventor: Yonatan Ushpizin, Glil Yam (IL)

(73) Assignee: Mazor Robotics Ltd., Caesarea (IL)

( * ) Notice: Subject to any disclaimer, the term of this patent is extended or adjusted under 35 U.S.C. 154(b) by 174 days.

(21) Appl. No.: 17/163,880

(22) Filed: Feb. 1, 2021

(65) Prior Publication Data

US 2022/0240967 A1    Aug. 4, 2022

(51) Int. Cl.
*A61B 17/32* (2006.01)
*A61B 17/16* (2006.01)
*A61B 34/30* (2016.01)
*A61B 17/00* (2006.01)

(52) U.S. Cl.
CPC ........ *A61B 17/32002* (2013.01); *A61B 17/16* (2013.01); *A61B 17/1604* (2013.01); *A61B 17/1671* (2013.01); *A61B 34/30* (2016.02); *A61B 2017/00261* (2013.01); *A61B 2017/32006* (2013.01); *A61B 2017/320008* (2013.01)

(58) Field of Classification Search
CPC .............. A61B 17/32002; A61B 17/16; A61B 17/1604; A61B 17/1671; A61B 34/30; A61B 2017/00261; A61B 2017/320008; A61B 2017/32006
See application file for complete search history.

(56) References Cited

U.S. PATENT DOCUMENTS

| | | | |
|---|---|---|---|
| 4,953,690 A | 9/1990 | Herzke | |
| 5,725,530 A | 3/1998 | Popken | |
| 5,919,203 A * | 7/1999 | Husted | A61B 17/32002 606/177 |
| 6,267,759 B1 * | 7/2001 | Quick | A61B 18/14 204/620 |
| 7,189,240 B1 | 3/2007 | Dekel | |
| 9,011,455 B2 | 4/2015 | Johnson et al. | |
| 9,095,345 B2 | 8/2015 | Linares et al. | |
| 9,668,747 B2 | 6/2017 | Metzger et al. | |
| 9,848,853 B2 | 12/2017 | Mitragotri et al. | |

(Continued)

FOREIGN PATENT DOCUMENTS

| | | |
|---|---|---|
| CN | 103705275 | 2/2016 |
| CN | 108498133 | 9/2018 |

(Continued)

*Primary Examiner* — Kevin T Truong
*Assistant Examiner* — Diana Jones
(74) *Attorney, Agent, or Firm* — Sheridan Ross P.C.

(57) ABSTRACT

A tool for cleaning a vertebral disc includes an elongated hollow shaft including a proximal end and a distal end; a first drum rotatably disposed in a housing secured to the proximal end of the shaft, the first drum having a first axis; a second drum rotatably disposed proximate the distal end of the shaft, the second drum having a second axis parallel to the first axis; and a belt extending through the hollow shaft and operatively coupled to the first drum and the second drum, the belt comprising a plurality of teeth configured to cut anatomical tissue, each tooth of the plurality of teeth remaining flush with an outer surface of the belt when a section of the belt comprising the tooth is substantially straight, and projecting beyond the outer surface when the section of the belt bends around the first drum or the second drum.

20 Claims, 7 Drawing Sheets

(56) References Cited

U.S. PATENT DOCUMENTS

| | | |
|---|---|---|
| 9,980,750 B2 | 5/2018 | Ali |
| 10,052,116 B2 | 8/2018 | Wallace et al. |
| 10,335,184 B2 | 7/2019 | Locke |
| 10,639,056 B2 | 5/2020 | Pell et al. |
| 2007/0167966 A1* | 7/2007 | Simpson ............ A61B 17/3211 606/180 |
| 2008/0033443 A1 | 2/2008 | Sikora et al. |
| 2009/0062802 A1* | 3/2009 | Palmer .................. B23D 61/18 606/171 |
| 2009/0118709 A1* | 5/2009 | Sand ................ A61B 17/32002 604/540 |
| 2009/0182361 A1* | 7/2009 | Thompson ..... A61B 17/320758 606/159 |
| 2009/0182362 A1* | 7/2009 | Thompson ..... A61B 17/320758 606/159 |
| 2010/0298833 A1 | 11/2010 | Smith |
| 2014/0148835 A1* | 5/2014 | Schmitz ........... A61B 17/32002 606/170 |
| 2017/0172586 A1 | 6/2017 | Wallace et al. |
| 2019/0239901 A1 | 8/2019 | Couture et al. |
| 2019/0282258 A1* | 9/2019 | Smith ................ A61B 17/1631 |
| 2020/0375625 A1* | 12/2020 | Baril .................. A61B 17/3205 |

FOREIGN PATENT DOCUMENTS

| | | |
|---|---|---|
| FR | 2886839 | 7/2008 |
| JP | 2004-065380 | 3/2004 |

* cited by examiner

DISC CLEANING SURGICAL TOOL

FIELD

The present technology generally relates to surgical tools, and more particularly relates to a disc cleaning tool.

BACKGROUND

Various tools may be used during surgery to cut and remove anatomical tissue during a surgical procedure. Robots may be used to assist with such surgical procedures. Robot-assisted surgeries may be completed semi-autonomously, with a surgeon controlling the robot (whether directly or indirectly) and/or a tool supported by the robot, or autonomously, with the robot operating the tool and completing the surgery without surgeon input.

SUMMARY

Example aspects of the present disclosure include:

A tool for cleaning a vertebral disc according to at least one embodiment of the present disclosure comprises an elongated hollow shaft comprising a proximal end and a distal end; a first drum rotatably disposed in a housing secured to the proximal end of the shaft, the first drum having a first axis; a second drum rotatably disposed proximate the distal end of the shaft, the second drum having a second axis parallel to the first axis; and a belt extending through the hollow shaft and operatively coupled to the first drum and the second drum, the belt comprising a plurality of teeth configured to cut anatomical tissue, wherein each tooth of the plurality of teeth remains flush with an outer surface of the belt when a section of the belt comprising the tooth is substantially straight, and projects beyond the outer surface when the section of the belt bends around the first drum or the second drum.

Any of the aspects herein, wherein the first drum is configured to drive the belt, and wherein the second drum is freely rotatable.

Any of the aspects herein, wherein the plurality of teeth are formed from a plurality of C-shape cuts in the belt.

Any of the aspects herein, wherein the plurality of teeth are offset to alternating sides of the belt.

Any of the aspects herein, wherein the housing comprises an irrigation system and a suction system.

Any of the aspects herein, wherein at least one portion of the belt is made from stainless steel.

Any of the aspects herein, further comprising a motor, the motor configured to drive at least one of the first drum and the second drum.

Any of the aspects herein, wherein at least one of the irrigation system and the suction system is disposed proximate to the second drum.

Any of the aspects herein, wherein each tooth of the plurality of teeth is configured to grasp anatomical tissue between the tooth and the first surface of the belt when the portion of the belt comprising the tooth is substantially straight, and release the anatomical tissue when the section of the belt comprising the tooth bends around the second drum.

A device for cleaning a vertebral disc according to at least one embodiment of the present disclosure comprises a housing; a first rotatable cylinder disposed in a first axial orientation within and proximate a proximal end of the housing; a second rotatable cylinder disposed outside a distal end of the housing in the first axial orientation; a belt extending between and operatively coupled to the first rotatable cylinder and the second rotatable cylinder, the belt comprising a plurality of cutting tabs, wherein each cutting tab of the plurality of cutting tabs remains flush with an outer surface of the belt when a section of the belt comprising the cutting tab is substantially straight, and projects beyond the outer surface when the section of the belt bends around the first rotatable cylinder or the second rotatable cylinder.

Any of the aspects herein, wherein the belt is a chain.

Any of the aspects herein, wherein the plurality of cutting tabs are formed from a plurality of C-shape cuts in the belt.

Any of the aspects herein, wherein the housing comprises a hollow shaft extending at least partially from the distal end toward the proximal end.

Any of the aspects herein, further comprising an irrigation system and a suction system, wherein the irrigation system comprises a fluid conduit configured to dispense a fluid onto at least one surface of the belt within the housing.

Any of the aspects herein, wherein the fluid conduit dispenses the fluid radially from within the first cylinder.

Any of the aspects herein, wherein the suction system comprises a conduit configured to remove anatomical tissue from the housing.

Any of the aspects herein, wherein the first rotatable cylinder has a larger diameter than the second rotatable cylinder.

Any of the aspects herein, wherein the plurality of cutting tabs are formed from a plurality of triangle-shape cuts.

A system for removing anatomical tissue from a vertebral disc according to at least one embodiment of the present disclosure comprises a cutting device comprising an elongated hollow shaft comprising a proximal end and a distal end; a first drum rotatably disposed in a housing secured to the proximal end of the shaft, the first drum having a first axis; a second drum rotatably disposed proximate the distal end of the shaft, the second drum having a second axis parallel to the first axis; and a belt extending through the hollow shaft and operatively coupled to the first drum and the second drum, the belt comprising a plurality of teeth configured to cut anatomical tissue, wherein each tooth of the plurality of teeth remains flush with an outer surface of the belt when a section of the belt comprising the tooth is substantially straight, and projects beyond the outer surface when the section of the belt bends around the first drum or the second drum; a drive system operably connected to the first drum and configured to rotate the first drum about the first axis; a fluid system configured to dispense into the housing; and a suction system configured to remove fluid and anatomical tissue from within the housing.

Any of the aspects herein, wherein the plurality of teeth are formed from a plurality of C-shape cuts in the belt.

Any aspect in combination with any one or more other aspects.

Any one or more of the features disclosed herein.

Any one or more of the features as substantially disclosed herein.

Any one or more of the features as substantially disclosed herein in combination with any one or more other features as substantially disclosed herein.

Any one of the aspects/features/embodiments in combination with any one or more other aspects/features/embodiments.

Use of any one or more of the aspects or features as disclosed herein.

It is to be appreciated that any feature described herein can be claimed in combination with any other feature(s) as described herein, regardless of whether the features come from the same described embodiment.

The details of one or more aspects of the disclosure are set forth in the accompanying drawings and the description below. Other features, objects, and advantages of the techniques described in this disclosure will be apparent from the description and drawings, and from the claims.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. When each one of A, B, and C in the above expressions refers to an element, such as X, Y, and Z, or class of elements, such as $X_1$-$X_n$, $Y_1$-$Y_m$, and $Z_1$-$Z_o$, the phrase is intended to refer to a single element selected from X, Y, and Z, a combination of elements selected from the same class (e.g., $X_1$ and $X_2$) as well as a combination of elements selected from two or more classes (e.g., $Y_1$ and $Z_o$).

The term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

Numerous additional features and advantages of the present invention will become apparent to those skilled in the art upon consideration of the embodiment descriptions provided hereinbelow.

BRIEF DESCRIPTION OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure can be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

DETAILED DESCRIPTION

It should be understood that various aspects disclosed herein may be combined in different combinations than the combinations specifically presented in the description and accompanying drawings. It should also be understood that, depending on the example or embodiment, certain acts or events of any of the processes or methods described herein may be performed in a different sequence, and/or may be added, merged, or left out altogether (e.g., all described acts or events may not be necessary to carry out the disclosed techniques according to different embodiments of the present disclosure). In addition, while certain aspects of this disclosure are described as being performed by a single module or unit for purposes of clarity, it should be understood that the techniques of this disclosure may be performed by a combination of units or modules associated with, for example, a computing device and/or a medical device.

In one or more examples, the described methods, processes, and techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors (e.g., Intel Core i3, i5, i7, or i9 processors; Intel Celeron processors; Intel Xeon processors; Intel Pentium processors; AMD Ryzen processors; AMD Athlon processors; AMD Phenom processors; Apple A10 or 10X Fusion processors; Apple A11, A12, A12X, A12Z, or A13 Bionic processors; or any other general purpose microprocessors), application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Before any embodiments of the disclosure are explained in detail, it is to be understood that the disclosure is not limited in its application to the details of construction and the arrangement of components set forth in the following description or illustrated in the drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, the present disclosure may use examples to illustrate one or more aspects thereof. Unless explicitly stated otherwise, the use or listing of one or more examples (which may be denoted by "for example," "by way of example," "e.g.," "such as," or similar language) is not intended to and does not limit the scope of the present disclosure.

To accomplish the task of successfully cutting and removing anatomical tissue, such as that from intervertebral discs, various types of surgical cutting tools may be used. Surgical cutting tools may clean the disc by repeatedly entering a disc space, cutting anatomical tissue, and exiting the disc space. A cleaning system, such as a suction tool, may be used in conjunction with the cutting tool to remove cut anatomical tissue. Suction is limited to the size of the disc space, so smaller spaces prevent the use of powerful suction systems, reducing the effectiveness of suction at the surgical site.

In some embodiments of the present disclosure, a chain-saw-like disc cleaning tool may be provided to remove anatomical tissue from a spine disc. The cleaning tool may include a suction device for extracting the cut anatomical tissue to prevent clogging of the cleaning tool. The cleaning tool may include a belt with a plurality of teeth formed from one or more cuts in the belt. The teeth may be configured to cut anatomical tissue and may be offset from one another to alternating sides of the belt. The teeth may be formed such that the teeth remain flush with the belt when the belt is substantially straight and may pop out from the belt when the belt bends (such as when the belt wraps around a pulley, drum, and/or circularly shaped object).

The teeth may pop out and cut anatomical tissue. The rotational movement of the teeth around the drum may cause the teeth to cut through the anatomical tissue and grasp the cut anatomical tissue between the tooth and a surface of the belt. The grasping may pin the anatomical tissue in place relative to the belt, preventing it from falling out or remaining in the surgical site. The belt may then move the anatomical tissue back through the cleaning device (e.g., through a shaft and into a housing). When in the housing, the belt may bend around another drum, causing the teeth to pop out or otherwise extend again. The popping out of the teeth may release the anatomical tissue from the belt, allowing it to be deposited in the housing.

The cleaning tool may also make use of an irrigation system and a suction system. The irrigation and suction system may remove the deposited anatomical tissue from the housing. For instance, the irrigation system may spray radially outward from proximate a center of a drum in the housing, facilitating removal of any anatomical tissue remaining on the teeth and/or the belt. The suction system may provide suction to remove anatomical tissue and/or carrier fluids from the irrigation system.

Existing tools for use in cleaning intervertebral disc spaces require repeated insertion and removal of the tool from the disc space. Such repeated insertion and removal can be difficult for a robotic system, particularly when the robotic system is operating autonomously. Tools according to embodiments of the present disclosure only require a single insertion into an intervertebral disc space, after which the tool can be operated to remove anatomical tissue from the disc space using a chain with teeth or blades that stretch into the disc space during rotation around a drum or other circular object (which changes the bending radius of the chain and thus causes a temporary change in the shape of the blades or teeth relative to the body of the chain). The teeth or blades are therefore able to cut tissue inside the intervertebral space and then extract the tissue and expel it outside the patient.

Figure 1:
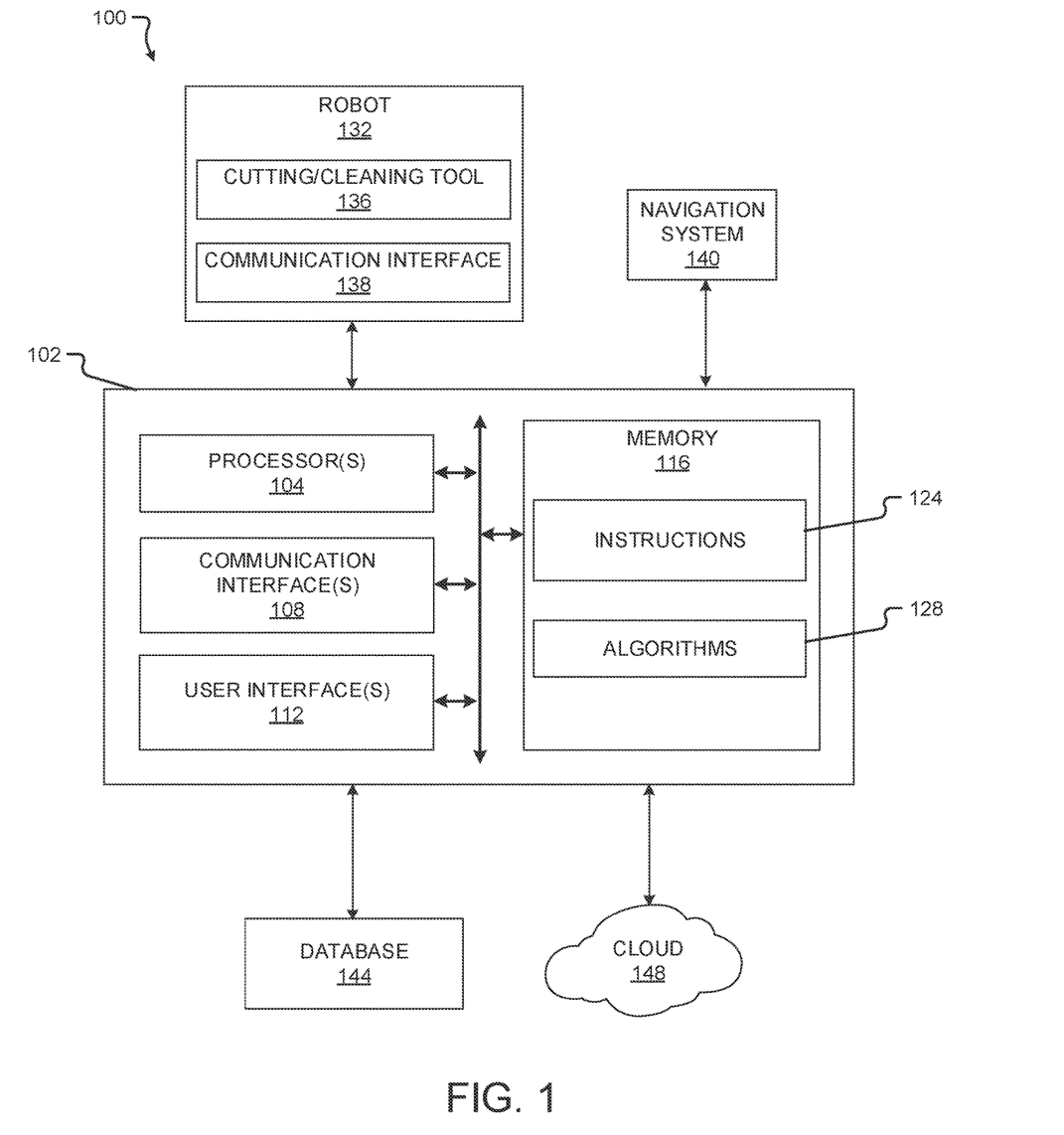
FIG. 1 is a block diagram of a system according to at least one embodiment of the present disclosure.
Figure 2:
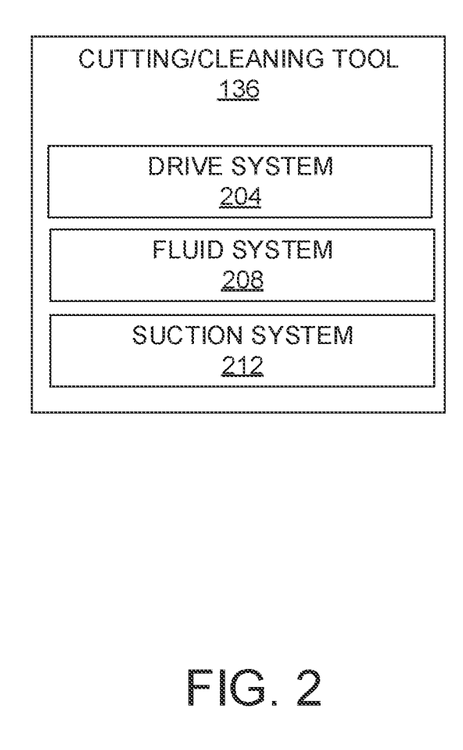
FIG. 2 shows a block diagram of components of a cutting and cleaning tool according to at least one embodiment of the present disclosure.

Turning first to FIGS. 1 and 2, aspects of a system 100 according to at least one embodiment of the present disclosure are shown. The system 100 may be used, for example, to carry out a procedure utilizing a cutting and cleaning surgical tool as described herein, or to gather information relevant to such a procedure; to improve patient outcomes in connection with a surgical procedure or task; or for any other useful purpose. The system 100 comprises a computing device 102, a robot 132, a navigation system 140, a database 144, and a cloud 148.

Notwithstanding the foregoing, systems according to other embodiments of the present disclosure may omit any one or more of the navigation system 140, database 144 and/or the cloud 148. Additionally, systems according to embodiments of the present disclosure may arrange one or more components of the system 100 differently (e.g., the cutting and cleaning tool 136 may comprise one or more components of the computing device 102, and/or vice versa), and/or include additional components not shown.

The computing device 102 comprises at least one processor 104, at least one communication interface 108, at least one user interface 112, and at least one memory 116. A computing device according to other embodiments of the present disclosure may omit one or both of the communication interface(s) 108 and/or the user interface(s) 112.

The at least one processor 104 of the computing device 102 may be any processor identified or described herein or any similar processor. The at least one processor 104 may be configured to execute instructions 124 stored in the at least one memory 116, which instructions 124 may cause the at least one processor 104 to carry out one or more computing steps utilizing or based on data received, for example, from the robot 132, the database 144, the cloud 148, combinations thereof, and/or components or subcomponents thereof. The instructions 124 may also cause the at least one processor 104 to utilize one or more algorithms 128 stored in the memory 116. In some embodiments, the at least one processor 104 may be used to control the robot 140 and/or a cutting and cleaning tool 136 during a surgical procedure, including during a procedure being carried out autonomously or semi-autonomously by the robot 132 using the cutting and cleaning tool 136.

The computing device 102 may also comprise at least one communication interface 108. The at least one communication interface 108 may be used for receiving sensor data (e.g., from the robot 132), a surgical plan or other planning data, or other information from an external source (such as the robot 132, the cutting and cleaning tool 136, the database 144, the cloud 148, and/or a portable storage medium (e.g., a USB drive, a DVD, a CD)), and/or for transmitting instructions, images, or other information from the at least one processor 104 and/or the computing device 102 more generally to an external system or device (e.g., another computing device 102, the robot 132, the cutting and cleaning tool 136, the database 144, the cloud 148, a drive system 204, an irrigation system 208, a suction system 212, and/or a portable storage medium (e.g., a USB drive, a DVD, a CD)). The at least one communication interface 108 may comprise one or more wired interfaces (e.g., a USB port, an ethernet port, a Firewire port) and/or one or more wireless interfaces (configured, for example, to transmit information via one or more wireless communication protocols such as 802.11a/b/g/n, Bluetooth, Bluetooth low energy, NFC, ZigBee, and so forth). In some embodiments, the at least one communication interface 108 may be useful for enabling the computing device 102 to communicate with one or more other processors 104 or computing devices 102, whether to reduce the time needed to accomplish a computing-intensive task or for any other reason.

The at least one user interface 112 may be or comprise a keyboard, mouse, trackball, monitor, television, touchscreen, button, joystick, switch, lever, and/or any other device for receiving information from a user and/or for providing information to a user of the computing device 102. The at least one user interface 112 may be used, for example, to receive a user selection or other user input; to receive a user selection or other user input regarding one or more configurable settings of the computing device 102, the robot 132, the cutting and cleaning tool 136, and/or any other component of the system 100; to receive a user selection or other user input regarding how and/or where to store and/or transfer data received, modified, and/or generated by the computing device 102; and/or to display information (e.g., text, images) and/or play a sound to a user based on data received, modified, and/or generated by the computing device 102.

Although the at least one user interface 112 is shown as part of the computing device 102, in some embodiments, the computing device 102 may utilize a user interface 112 that is housed separately from one or more remaining components of the computing device 102. In some embodiments, the user interface 112 may be located proximate one or more other components of the computing device 102, while in other embodiments, the user interface 112 may be located remotely from one or more other components of the computer device 102.

The at least one memory 116 may be or comprise RAM, DRAM, SDRAM, other solid-state memory, any memory described herein, or any other tangible non-transitory memory for storing computer-readable data and/or instructions. The at least one memory 116 may store, for example, instructions 124 and/or algorithms 128. In some embodiments, the memory 116 may also store one or more preoperative and/or other surgical plans; one or more images of one or more patients, including in particular of an anatomical feature of the one or more patients on which one or more surgical procedures is/are to be performed; data received from the cutting and cleaning tool 136 (including any component thereof) or elsewhere; and/or other information useful in connection with the present disclosure.

The instructions 124, as described above, may be or comprise any instructions for execution by the at least one processor 104 that cause the at least one processor to carry out one or more steps of any of the methods described herein. The instructions 124 may be or comprise instructions for carrying out a procedure, or for manipulating a robot such as the robot 132 to carry out the same; instructions for determining a rotation rate of one or more cylindrical drums in a surgical tool; instructions for control of irrigation and/or suction systems; or otherwise. The instructions 124 may additionally or alternatively enable the at least one processor 104, and/or the computing device 102 more generally, to increase the likelihood of a positive procedural outcome during any surgical procedure in which information obtained from a surgical tool as described herein may be relevant.

The algorithms 128 may be or comprise any algorithms useful for converting sensor data received from the robot 132 into information useful by a processor 104, a robotic control system, or otherwise (e.g., a rotation rate of cylindrical drums in a surgical tool, a calculated force value, a pressure value, a distance measurement). The algorithms 128 may further be or comprise algorithms useful for controlling the robot 132. The algorithms 128 may further be or comprise any algorithms useful for generating one or more recommendations to a surgeon or other user of the system 100 based on information received from a robot 132, and/or for modifying a preoperative or other surgical plan based on such information and/or an evaluation of such information. The algorithms 128 may further be or comprise algorithms useful for controlling the robot 132 and/or the cutting and cleaning tool 136. In some embodiments, the algorithms 128 may be or include machine learning algorithms and/or algorithms useful for analyzing historical data (e.g., stored in a database such as database 144).

The database 144 may store any information that is shown in FIGS. 1 and 2 and/or described herein as being stored in the memory 116, including instructions such as the instructions 124 and/or algorithms such as the algorithms 128. In some embodiments, the database 144 stores one or more preoperative or other surgical plans. The database 144 may additionally or alternatively store, for example, information about or corresponding to one or more characteristics of one or more of a robot such as the robot 132, a surgical tool such as the cutting and cleaning tool 136, the navigation system 140, and/or other information regarding available tools and/or equipment for use in connection with a surgical procedure. The database 144 may be configured to provide any such information to the robot 132, a cutting and cleaning tool 136, or to any other device of the system 100 or external to the system 100, whether directly or via the cloud 148. In some embodiments, the database 144 may be or comprise part of a hospital image storage system, such as a picture archiving and communication system (PACS), a health information system (HIS), and/or another system for collecting, storing, managing, and/or transmitting electronic medical records including image data. Also in some embodiments, the memory 116 may store any of the information described above.

The cloud 148 may be or represent the Internet or any other wide area network. The computing device 102 may be connected to the cloud 148 via the communication interface 108, using a wired connection, a wireless connection, or both. In some embodiments, the computing device 102 may communicate with the database 144 and/or an external device (e.g., a computing device) via the cloud 148.

The navigation system 140 may provide navigation for a surgeon and/or for the robot 132 and/or components thereof during an operation or surgical procedure. The navigation system 140 may be any now-known or future-developed navigation system, including, for example, the Medtronic StealthStation™ S8 surgical navigation system. The navigation system 140 may include a camera or other sensor(s) for detecting and/or tracking one or more reference markers, navigated trackers, or other objects (e.g., a plurality of tracking markers) within an operating room or other room where a surgical procedure takes place. In some embodiments, the navigation system 140 may comprise the plurality of sensors. In various embodiments, the navigation system 140 may be used to track a position of the robot 132, and/or of one or more other objects to which the navigation system 140 has a line of sight (where the navigation system is an optical system) or that are otherwise detectable by the navigation system 140. The navigation system 140 may be used to track a position of one or more reference markers or arrays or other structures useful for detection by a camera or other sensor of the navigation system 140. The navigation system 140 may include a display for displaying one or more images from an external source (e.g., the computing device 102, the cloud 148, or other source) or a video stream from the navigation camera or from another sensor. In some embodiments, the system 100 may operate without the use of the navigation system 140.

With continued reference to FIG. 2, a block diagram of the cutting and cleaning tool 136 according to at least one embodiment of the present disclosure is shown. These components include a drive system 204, a fluid system 208, and a suction system 212. Notwithstanding the foregoing, systems according to other embodiments of the present disclosure may omit one or more components of the cutting and cleaning tool 136, arrange one or more components of the cutting and cleaning tool 136 differently (e.g., the drive system 204, the fluid system 208, and/or the suction system 212 may comprise one or more components of the computing device 102, and/or vice versa, or one or more of the drive system 204, the fluid system 208, and/or the suction system 212 may comprise a separate system operably connectable to the cutting and cleaning tool 136 but not part of the cutting and cleaning tool 136), and/or include additional components not shown.

The cutting and cleaning tool 136 is configured to cut and remove anatomical tissue from a surgical site. The cutting and cleaning tool 136 may be comprise one or more of the drive system 204, the fluid system 208, and the suction system 212, as shown in FIG. 2, or may be operably connected to one or more of the foregoing systems. The drive system 204 is configured to drive (e.g., provide mechanical power to) one or more components of the cutting and cleaning tool 136. The drive system 204 may comprise a motor that turns a shaft of the cutting and cleaning tool 136. The motor may be powered by electricity or any other suitable form of energy. In some embodiments, the drive system 204 may comprise a motor (not shown) that is operatively connected to the cutting and cleaning tool 136. The motor may drive the cutting and cleaning tool 136 by causing rotary motion of a shaft (e.g., a drive shaft 316) disposed on a proximal end of the cutting and cleaning tool 136, which in turn causes rotational movement of a drum (e.g., a proximal end drum 328) and translation of a belt (e.g., a belt 310) to perform a cutting action. In some embodiments, the motor may be operatively connected to additional and/or alternative drums (e.g., a distal end drum 324). As used above and herein, the term "proximal end" refers to the end of a tool or part, or to a location, that is or would be proximate an operator or user of the tool or part during use thereof, and the term "distal end" or "working end" refers to the end of the tool or part, or to a location, that is or would be proximate a patient during use of the tool or part.

In some embodiments, the motor used by the drive system 204 may be selected in type and design to best match the requirements of the surgery being performed by the cutting and cleaning tool 136. Some non-limiting examples of motor types that may be used include a DC brushed motor, an AC or DC brushless motor, a direct drive motor, a servo motor, a stepper motor, a turbine motor, a pneumatic motor, or the like. In some embodiments, the drive system 204 may use one or more gears or other mechanical devices (e.g., a gear and chain, a rack and pinion) to convert rotational motion (e.g., of components of the cutting and cleaning tool 136) into translational motion, and/or vice versa. In some embodiments, the drive system 204 may be controlled manually (e.g., by a surgeon), semi-automatically (e.g. by a robot guided by a surgeon), or automatically (e.g., by a robot). For instance, the surgeon and/or the robot may input commands (e.g., through the user interface 112 in case of the surgeon and through the one or more algorithms 140 for the robot) to alter, adjust, or otherwise change the power delivered by the motor to the cutting and cleaning tool 136. In some embodiments, the drive system 204 may be operatively connected to other components of the cutting and cleaning tool 136 (e.g., to the fluid system 208 and/or the suction system 212). In such embodiments, the motor of the drive system 204 may be simultaneously used to operate the fluid system 208 and/or the suction system 212.

The fluid system 208 is configured to irrigate the cutting and cleaning tool 136 and/or components thereof. The fluid system 208 may comprise one or more fluid reservoirs and a fluid conduit (e.g., an irrigation conduit 336). The fluid reservoirs may store one or more fluids (e.g., saline, water, etc.) that are capable of being transferred to the cutting and cleaning tool 136 before, during, and/or after a surgical procedure. The one or more fluids may be fluidically communicated to the cutting and cleaning tool 136 through a fluid conduit (e.g., through an irrigation conduit 336). The fluids stored in the fluid reservoirs and used in the cutting and cleaning tool 136 may serve a variety of purposes, such as to lubricate one or more components of the cutting and cleaning tool 136 and/or to assist in flushing out anatomical tissue from the cutting and cleaning tool 136. For example, the cutting of anatomical tissue by the cutting and cleaning tool 136 may leave anatomical tissue or residue thereof on one or more components of the cutting and cleaning tool 136 (e.g., on one or more cutting teeth 340, on a belt 310, on a proximal end drum 328, etc.), which may need to be removed to improve tool function (e.g., to prevent the cutting and cleaning tool 136 from clogging, to remove anatomical tissue from the one or more cutting teeth 340 so that they can continue to effectively cut). In such embodiments, the fluid system 208 may provide water or saline through a fluid conduit to the cutting and cleaning tool 136 to remove anatomical tissue from the components of the cutting and cleaning tool 136.

The suction system 212 is configured to provide a vacuum to remove anatomical tissue and/or other debris, whether entrained in fluid from the fluid system 208 or not, from the cutting and cleaning tool 136. The suction system 212 may include a motor (not shown) for generating a vacuum, as well as a container (not shown) for capturing the material removed from the cutting and cleaning tool 136. In some embodiments, the suction system 212 may make use of the same motor as the drive system 204, or of a similar motor. In some embodiments, the suction system 212 may be configured to turn on (e.g., begin generating a vacuum to remove anatomical tissue) when the drive system 204 and/or the irrigation system 208 are turned on. In some embodiments, the container for capturing the removed material may be configured to receive fluids (e.g., fluids from the irrigation system 208). As such, fluid released by the irrigation system 208, as well as any anatomical tissue removed from the components of the cutting and cleaning tool 136, may be removed from the cutting and cleaning tool 136 and collected in the container.

Figure 3A:
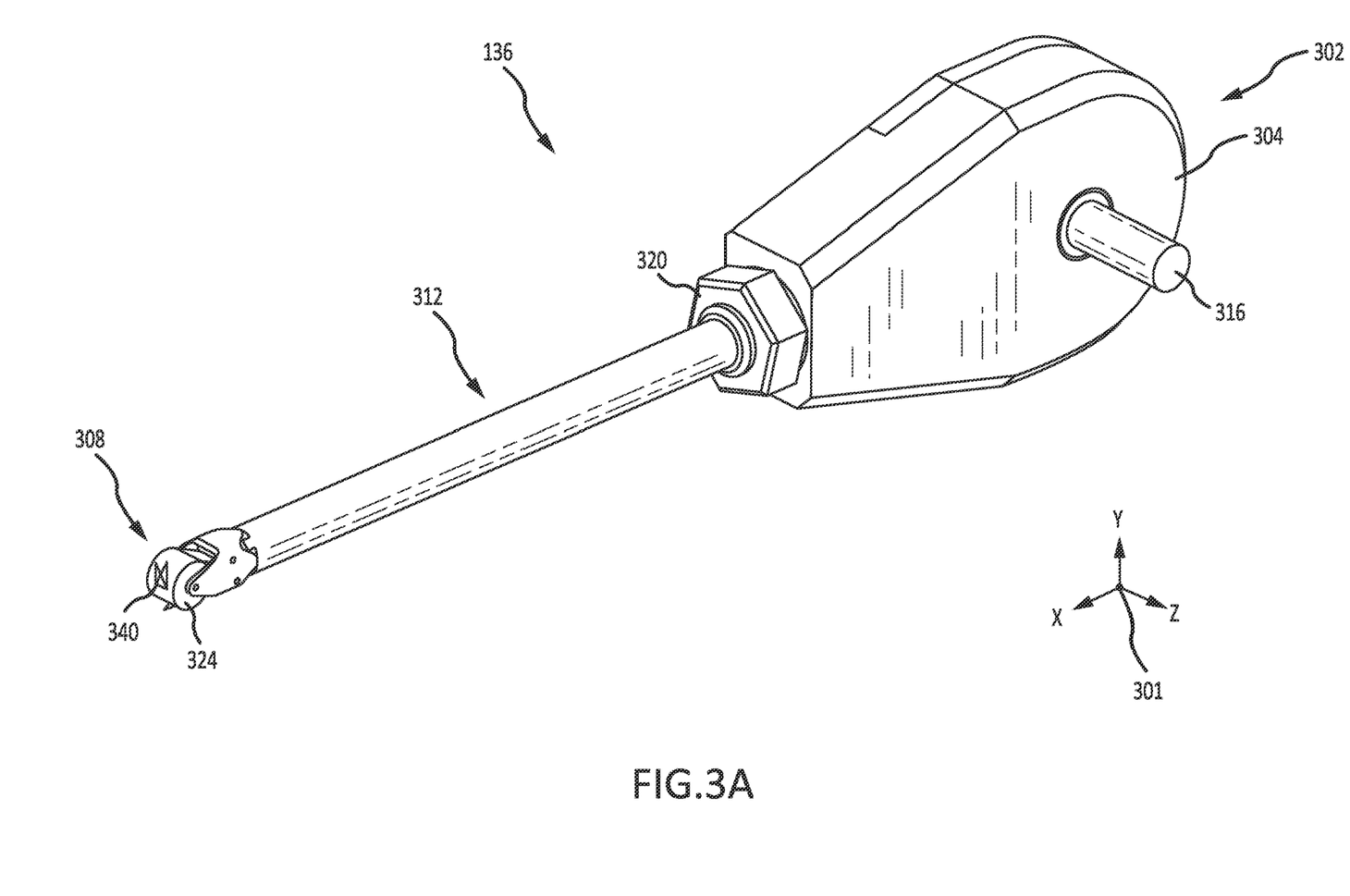
FIG. 3A shows a schematic view of a cutting and cleaning tool according to at least one embodiment of the present disclosure.
Figure 3B:
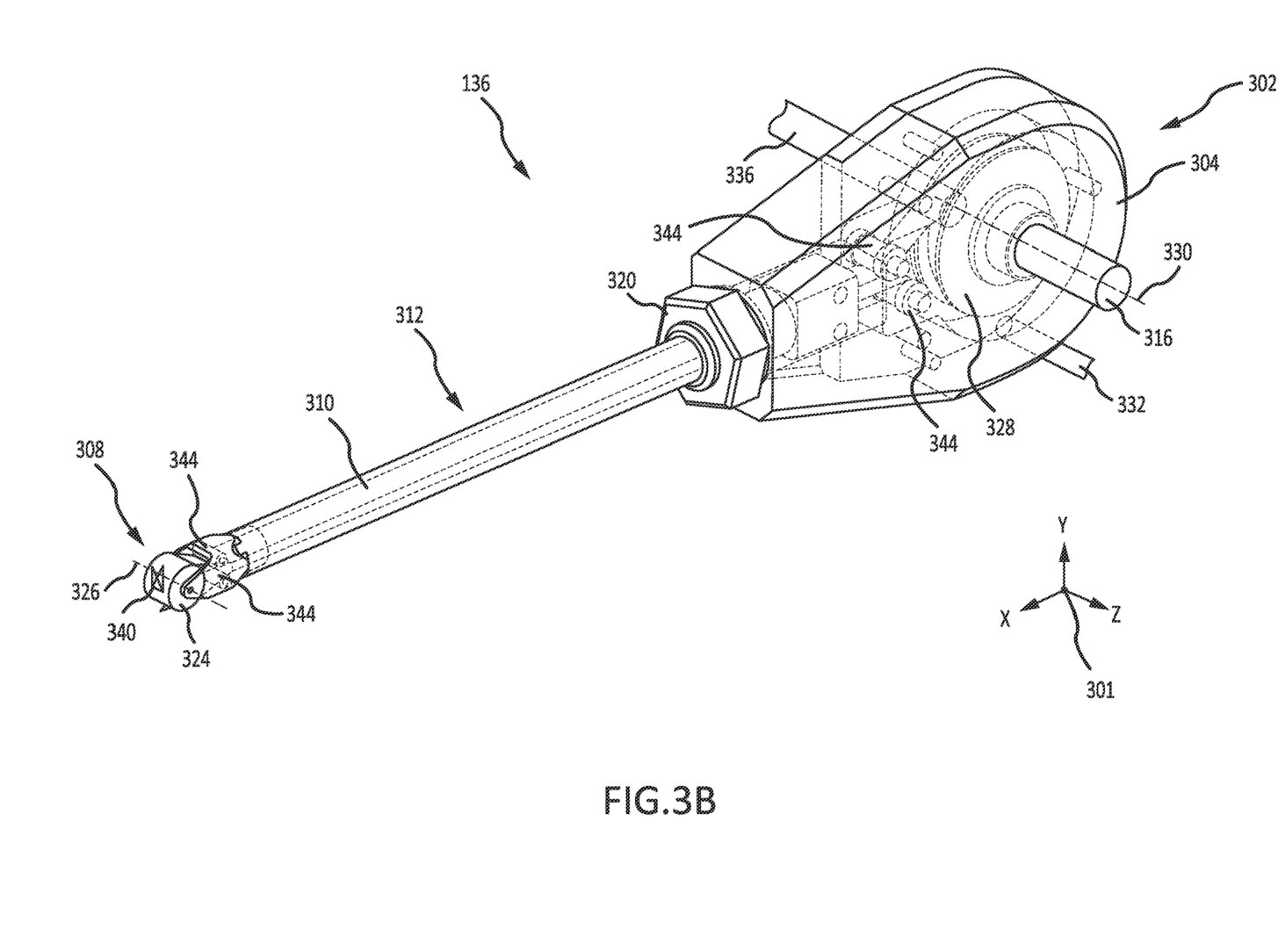
FIG. 3B shows a schematic view of internal components the cutting and cleaning tool according to at least one embodiment of the present disclosure.
Figure 3C:
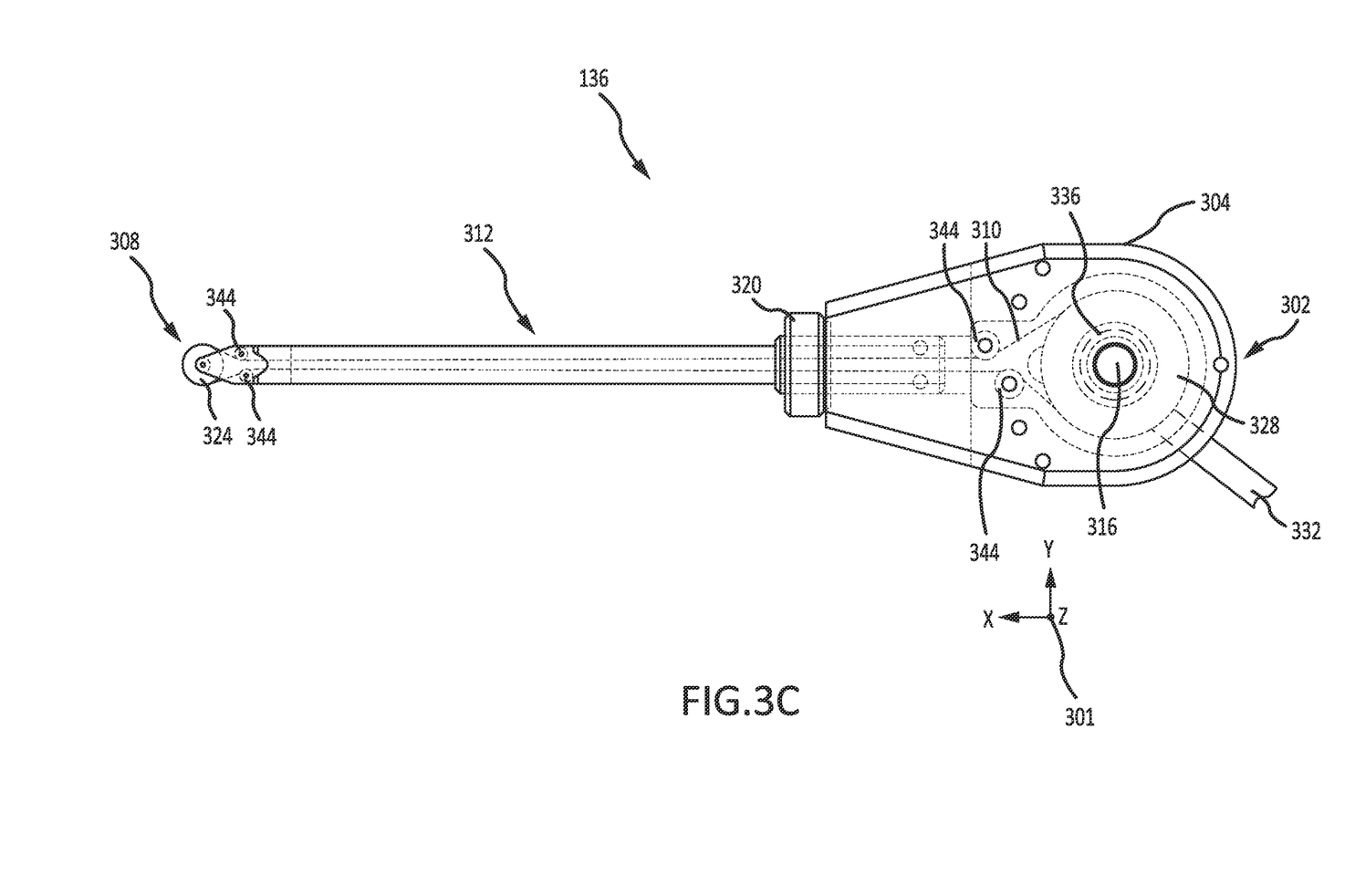
FIG. 3C is a side view of the cutting and cleaning tool according to at least one embodiment of the present disclosure.

Turning to FIGS. 3A-3C, various aspects of a cutting and cleaning tool 136 are shown in accordance with embodiments of the present disclosure. The cutting and cleaning tool 136 is designed to cut and remove anatomical tissue, such as during removal of a disc from an intervertebral space. The cutting and cleaning tool 136 may comprise one or more components previously described herein (e.g., a computing device 102, a drive system 204, etc.). The cutting and cleaning tool 136 depicted in FIGS. 3A-3C comprises a housing 304, a belt 310, an elongated shaft 312, a drive shaft 316, an attachment mechanism 320, a distal end drum 324, a proximal end drum 328, a suction conduit 332, and an irrigation conduit 336. The above notwithstanding, the cutting and cleaning tool 136 according to other embodiments of the present disclosure may omit one or more components of the cutting and cleaning tool 136, arrange one or more components of the cutting and cleaning tool 136 differently (e.g., the cutting and cleaning tool 136 may comprise one or more components of the computing device 102, and/or vice versa), and/or include additional components not shown.

The various views of the cutting and cleaning tool 136 are described with reference to a coordinate system 301. The coordinate system 301, as shown in FIGS. 3A-3C and 4A-4B, includes three dimensions comprising an X-axis, a Y-axis, and a Z-axis. Additionally or alternatively, the coordinate system 301 may be used to define planes (e.g., the XY-plane, the XZ-plane, and the YZ-plane) of the surgical tool 300. These planes may be disposed orthogonal, or 90 degrees, to one another. While the origin of the coordinate system 301 may be placed at any point on or near the surgical tool 300, for the purposes of description, the axes of the coordinate system 301 are disposed along the same directions from figure to figure. Additionally or alternatively, the directionality of the X-axis, Y-axis, and Z-axis may be flipped, as noted with negative directionality (e.g., the negative X-axis direction is the opposite direction of the X-axis direction illustrated by the direction of the associated arrow).

The housing 304 is disposed on a proximal end 302 of the cutting and cleaning tool 136 (e.g., a negative X-axis direction based on the coordinate system 301) and contains one or more components of the cutting and cleaning tool 136. For example, as depicted in FIG. 3B, the housing 304 may contain the proximal end drum 328, portions of the belt 310 and drive shaft 316, and portions of the suction conduit 332 and irrigation conduit 336. In some embodiments, the housing 304 may be disposed on a proximal end of the elongated shaft 312 (or vice versa), and/or may be connected thereto (e.g., using the attachment mechanism 320). The housing 304 may operate to ensure internal components of the housing 304 are housed safely (e.g., to avoid damage to the components inside the housing 304). The housing 304 may additionally comprise mechanical components configured to facilitate the use of the cutting and cleaning tool 136. For example, the housing 304 may contain guides and/or slotted portions to align the belt 310 to wrap around the proximal end drum 328. The housing 304 may include an attachment device (not shown) which may attach the cutting and cleaning tool 136 to a robot (e.g., a robot 132). The attachment device may be, for example, a clamp, screw-on system, or other attachment mechanism that affixes the cutting and cleaning tool 136 to the robot.

The belt 310 is configured to extend through the elongated shaft 312 and operatively couple the distal end drum 324 to the proximal end drum 328. The belt 310, distal end drum 324, and proximal end drum 328 thus act as a belt and pulley system. Power may be transferred between the belt 310 and either or both of the proximal end drum 328 and/or the distal end drum 324, or vice versa, by friction and/or by mechanical interaction (e.g., via interacting teeth on the belt 310 and the proximal end drum 328 and/or the distal end drum 324). The belt 310 is configured to transfer power between the distal end drum 324 and the proximal end drum 328 in response to rotational movement in at least one of the distal end drum 324 and the proximal end drum 328. For instance, in some embodiments, the proximal end drum 328 may be configured to rotate (e.g., rotate about an axis 330 parallel to the Z-axis of the coordinate system 301), which rotation may cause the belt 310 to move, which in turn may cause rotation of the distal end drum 324. The belt 310 may be made of a sturdy material (e.g., steel, galvanized steel, a rubber/steel composite, etc.) and may be resilient to damage or wear and tear associated with continued use. In some embodiments, the belt 310 may be made of the same material as the housing 304.

The proximal end drum 328 is positioned on or near a proximal end 302 of the cutting and cleaning tool 136 in the housing 304 and configured to rotate about an axis. The proximal end drum 328 may be a drum, cylinder, gear, or any other three-dimensional object capable of rotational movement about an axis (e.g., about the axis 330, in the XY-plane, etc.). In some embodiments, the drive shaft 316 may be operatively connected to a power source (e.g., a motor) which may cause rotational movement of the drive shaft 316. In some embodiments, the proximal end drum 328 may be operatively connected to a drive system (e.g., a drive system 204, or a drive system separate from but operably connectable to the cutting and cleaning tool 136). The drive system may cause rotational motion of the proximal end drum 328 using or via the drive shaft 316. The drive shaft 316 may be coupled with a motor (not shown) and configured to transfer torque from the motor to the proximal end drum 328. The resulting rotational movement of the drive shaft 316 may in turn cause rotational movement of the proximal end drum 328. In some embodiments, the cutting and cleaning tool 136 may omit a drive shaft 316 and may alternatively utilize an internal motor (not shown). The internal motor may be stored within the housing 304 and/or within the proximal end drum 328 and may cause rotational movement of the proximal end drum 328. The drive shaft may be made of a non-conductive material (e.g., plastic) to prevent inadvertent short circuiting and/or transfer of current between the motor and the cutting and surgical tool 136 and/or components thereof. In some embodiments, the proximal end drum 328 may be made of a material resistant to water damage and/or corrosion (e.g., stainless steel, galvanized steel, etc.).

In some embodiments, the rotational movement of the proximal end drum 328 may cause movement of the belt 310, while in other embodiments, rotational movement of the distal end drum 324 may cause movement of the belt 310. In some embodiments, the proximal end drum 328 may be larger in radius than the distal end drum 324, such that a rotational speed of the proximal end drum 328 may be different than a rotational speed of the distal end drum 324. The radius of curvature of the proximal end drum 328 and of the distal end drum 324 may be selected based factors such as an optimal or desired drive speed of a drive system 204, a desired rotational speed of the distal end drum 324, and/or a desired amount of extension of one or more cutting teeth 340 from the belt 310 proximate the proximal end drum 328 and the distal end drum 324. As will be appreciated based on the present disclosure, a first portion of the belt 310 travels in one direction through the elongated shaft 312 (e.g., from the proximal end drum 328 toward the distal end drum 324, or vice versa), while a second portion of the belt 310 travels in a second direction opposite the first direction through the elongated shaft 312.

In some embodiments, the housing 304 (and/or the elongated shaft 312) may contain additional pulleys, guides, and/or belt rollers to facilitate the movement of the belt 310.

For example, as shown in FIGS. 3B and 3C, tensioner or guide pulleys 344 maintain tension in the belt 310 (thus reducing a chance of the belt 310 slipping off of the proximal end drum 328 and/or the distal end drum 324) while also ensuring that the belt 310 is able to pass through the somewhat narrow elongated shaft 312. In some embodiments, the belt 310 may be made out of various materials, such as stainless steel, titanium, poly-paraphenylene terephthalamide (also known as Kevlar, which is a registered trademark of E. I. Du Pont de Nemours and Company), carbon fiber, other composite and/or polymer materials, combinations thereof, and/or the like.

The distal end drum 324 is positioned at or proximate a distal end 308 of the surgical tool 300 and configured to revolve about an axis 326. The distal end drum 324, while displayed as a drum in the accompanying figures, may be a cylinder, gear, or other three-dimensional shape capable of revolving about an axis. The axes 326 and 330 of the distal end drum 324 and the proximal end drum 328, respectively, are parallel, although in some embodiments the axes 326 and 330 may not be parallel. The distal end drum 324 may be freely rotatable. In other words, the distal end drum 324 may be a driven component (configured to be driven by the belt 310, which may in turn be driven by the proximal end drum 328) rather than a drive component. The distal end drum 324 may be moved by the belt 310. For example, frictional contact between the distal end drum 324 and the moving belt 310 may cause the distal end drum 324 to rotate. In some embodiments, the distal end drum 324 may not be rotatable, but the interface between the distal end drum 324 and the belt 310 may be characterized by a low coefficient of friction, such that the belt 310 can easily slide over the outer, circumferential surface of the distal end drum 324.

As noted above, the belt 310 extends around and between the proximal end drum 328 and the distal end drum 324. As a result, where the proximal end drum 328 acts as a drive pulley and the distal end drum 324 acts as a driven pulley, rotation of the proximal end drum 328 around the axis 330 in a first direction causes the belt 310 and the distal end drum 324 to also rotate in the first direction, while rotation of the proximal end drum 328 around the axis 330 in a second direction opposite the first direction causes the belt 310 and the distal end drum 324 to also rotate in the second direction. In some embodiments, the distal end drum 324 may operate as a drive pulley and the proximal end drum 328 may act as the driven pulley, or both the distal end drum 324 and the proximal end drum 328 may be either driven pulleys or drive pulleys.

The elongated shaft 312 may be fashioned of a material with sufficient strength and rigidity to prevent bending or deformation thereof due to squeezing or other forces imposed thereon by a patient's anatomy. Additionally, the elongated shaft 312 may comprise a tapered distal end to facilitate insertion thereof into a patient (whether through an incision, an MIS port, or otherwise). In some embodiments, the distal end drum 324 may be retractable within the elongated shaft 312 (or the elongated shaft 312 may be extendable over the distal end drum 324) to facilitate insertion of the distal end of the cutting and cleaning tool 136 into a patient, after which the distal end drum 324 and/or the shaft 312 may be returned to an operating position, as shown in FIGS. 3A-4B.

The attachment mechanism 320 may attach the elongated shaft 312 to the housing 304 (or vice versa). The attachment mechanism may be or comprise a screw and/or a nut. The attachment mechanism may comprise one or more seals or gaskets. The attachment of the elongated shaft 312 to the housing 304 may allow the distal end 308 of the cutting and cleaning tool 136 to extend from the housing 304 to better facilitate the cutting of anatomical tissue. In some embodiments, the attachment mechanism 320 may attach cutting and cleaning tool 136 to a robot (e.g., a robot 132). In such embodiments, the attachment mechanism 320 may secure the housing 304 or the elongated shaft 312 to a robot (e.g., to a robotic arm of a robot 132). The robot may then be used to manipulate the cutting and cleaning tool 136 to insert the distal end into an intervertebral disc space, with the elongated shaft 312 extending from the distal end 308 inside the patient to the housing 304 outside of the patient.

The cutting and cleaning tool 136 may comprise or be connected to a suction system 212 via a suction conduit 332. Through the suction conduit 332, the suction system 212 removes anatomical tissue, anatomical tissue residue, and/or fluids from the housing 304. In some embodiments, the suction conduit 332 may be made of a rigid and/or flexible material capable of maintaining its shape and structure while under vacuum. The suction conduit 332 may be connected to the housing 304 and may be used to create a vacuum in one or more internal portions of the housing 304. In some embodiments, the suction conduit 332 may be positioned near the proximal end drum 328 and may remove anatomical tissue and fluids on or near the proximal end drum 328 (e.g., anatomical tissue entrained in fluid sprayed within the housing 304 by a fluid system 208). In some embodiments, a suction system 212 may use the suction conduit 332 to apply a vacuum such that the internal components of the housing 304 all experience suction.

In some embodiments, the suction conduit 332 may be a component of a suction system (e.g., a suction system 212). The suction system 212 may be controlled autonomously (e.g., a computing device 102 may control the operation of the suction system 212), semi-autonomously (e.g., the surgeon controls the vacuum applied via the suction conduit 332 by regulating the suction system 212, or otherwise selects one or more operating settings of the suction system 212), or manually (e.g., the surgeon turns on and off and/or otherwise adjusts the settings of the suction system 212). The suction conduit 332 may connect to a container (not shown) for collecting anatomical tissue and/or other debris from the housing 304.

The irrigation conduit 336 may be operatively connected to the housing 304 and/or one or more components thereof (e.g., the proximal end drum 328) and configured to provide fluid for the purposes of cleaning anatomical tissue from the cutting and cleaning tool 136, and more specifically from the belt 310. For instance, the irrigation conduit 336 may carry water from a fluid reservoir into the housing 304, where the water may be sprayed onto the belt 310 and/or one or more components of the housing 304 to remove anatomical tissue (and/or anatomical fluids) therefrom. In one embodiment, the irrigation conduit 336 may be connected to an inner cavity (not shown) in the proximal end drum 328. In such embodiments, the proximal end drum 328 may comprise one or more holes on the outer, circumferential surface thereof, to permit water to escape. The irrigation conduit 336 may pump water into the proximal end drum 328, and the water may be sprayed from the proximal end drum 328 onto components of the housing 304 (e.g., sprayed onto the belt 310, in a direction that pushes anatomical tissue from the belt 310 into an open volume within the housing 304). In some embodiments, the spray of water may result from a pressure differential (e.g., the irrigation conduit 336 creates pressure to expel the water) and/or from the centrifugal force on the water created by the rotational motion of the proximal end drum 328. The water and any anatomical tissue entrained therein may then be evacuated from the housing 304 (e.g., via the suction conduit 332 or otherwise).

Figure 4A:
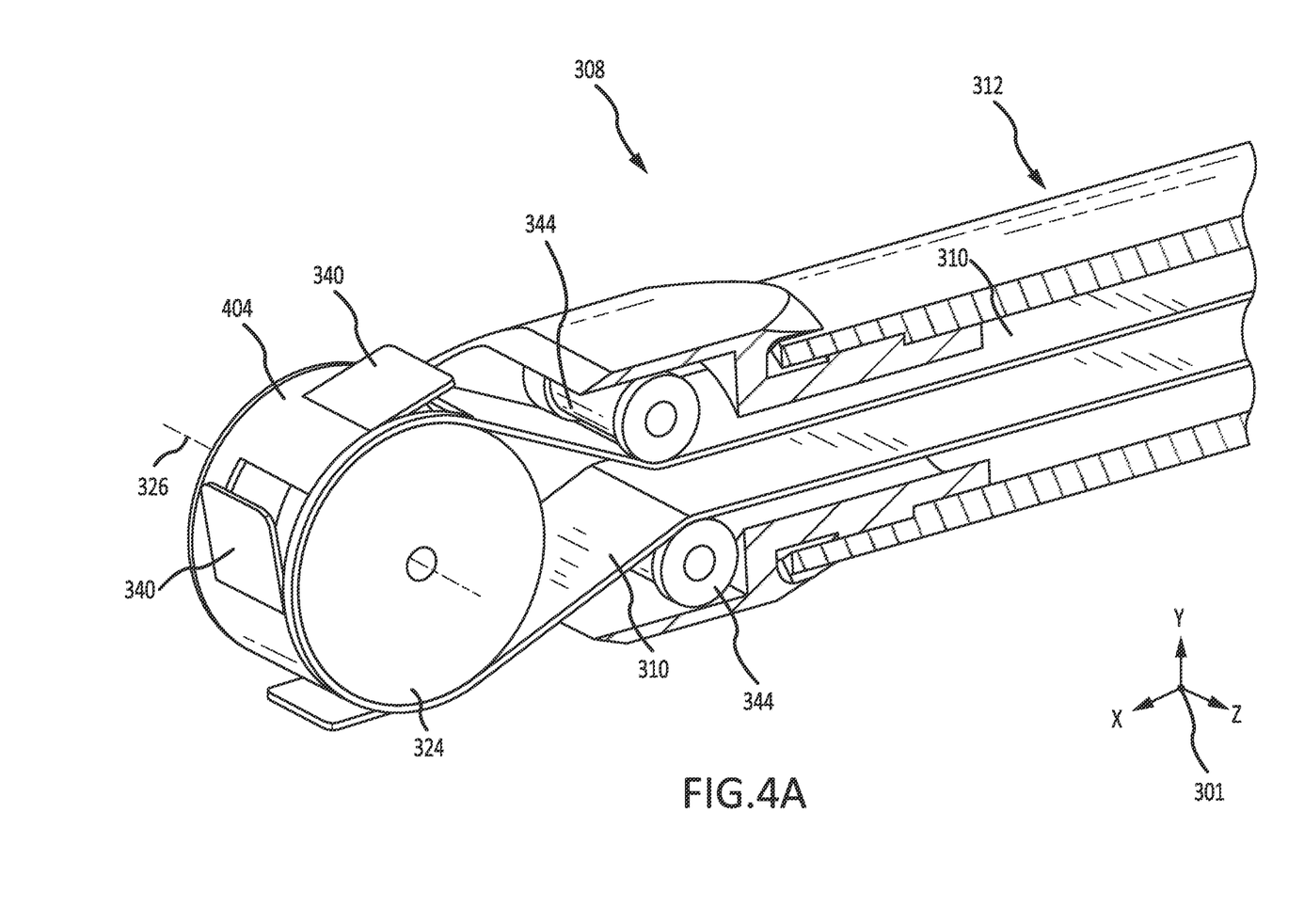
FIG. 4A illustrates a detailed schematic view of a distal end of the cutting and cleaning tool according to at least one embodiment of the present disclosure.
Figure 4B:
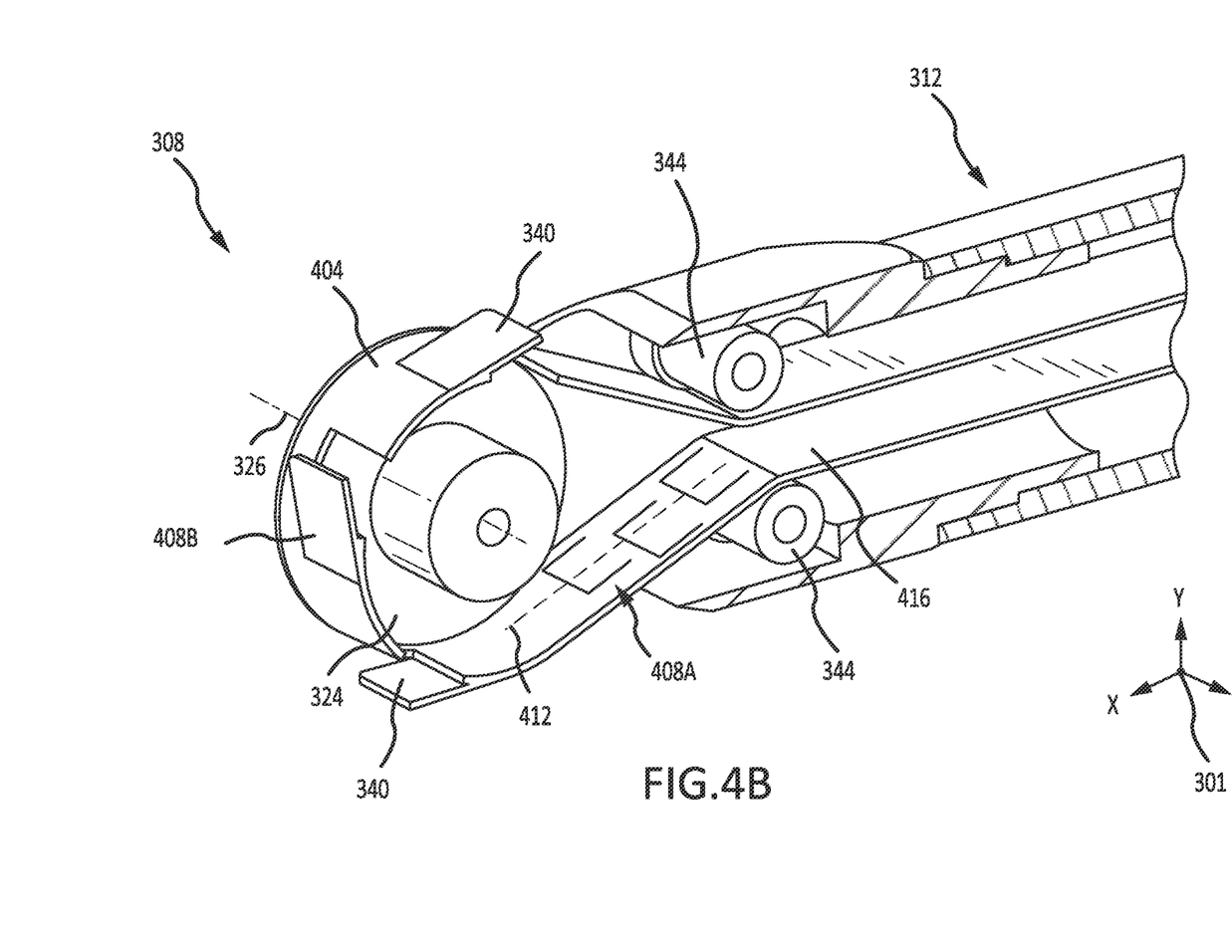
FIG. 4B illustrates a detailed schematic view of a distal end of the cutting and cleaning tool according to at least one embodiment of the present disclosure.

Turning to FIGS. 4A-4B, two close-up views of a distal end 308 of a cutting and cleaning tool 136 are shown in accordance with embodiments of the present disclosure. The distal end 308 may comprise a distal end drum 324 around which the belt 310 passes. One or more teeth 340 are cut into or otherwise provided on the belt 310, which teeth 340 extend from the belt 310 when the belt 310 curves around the distal end drum 324. Like the proximal end drum 328, the distal end drum 324 may be a drum, cylinder, gear, or other three-dimensional shape capable of rotational movement about an axis (e.g., an axis 326). The belt 310 extends through the elongated shaft 312 and wraps around an outside, circumferential surface of the distal end drum 324. In the embodiment depicted in FIG. 4A, the distal end drum 324 is positioned outside the distal end of the elongated shaft 312 (e.g., further along the X-axis direction) and is rotatably affixed to the elongated shaft 312. The attachment between the distal end drum 324 and the elongated shaft 312 may permit the distal end drum 324 to rotate freely (e.g., rotation of the distal end drum 324 about the axis 326 is not impeded by the elongated shaft 312). The belt 310 may contact the outside or circumferential surface of the distal end drum 324 such that rotational movement of the distal end drum 324 may cause translational movement of the belt 310, and/or vice versa.

The belt 310 comprises one or more teeth 340. The one or more teeth 340 may be configured to cut and remove anatomical tissue from a surgical site. In some embodiments, the one or more teeth 340 may be made from various materials designed to optimize the cutting of specific anatomical tissue. The one or more teeth 340 may be made from the same material or materials as the belt 310. The one or more teeth 340 may be configured to cut anatomical tissue from a spinal disc or any other anatomical location. The one or more teeth 340 may be fashioned from a plurality of cuts in the belt 310. For instance, the belt 310 may comprise one or more cuts (e.g., C-shape or U-shape cuts) that define the one or more teeth 340. Different types and shapes of cuts may be used to form the one or more teeth 340 for different surgical purposes. The cuts may be C-shape cuts that create tabs in the belt 310 (e.g., such that each tooth of the one or more teeth 340 is a tab-like structure) that are configured to cut anatomical tissue. In some embodiments, the one or more teeth 340 may be defined by triangle-shape cuts. The one or more teeth 340 may be filed or otherwise sharpened after being formed to improve cutting efficiency and effectiveness. In some embodiments, the one or more teeth 340 may be serrated.

The one or more teeth 340 are configured to be flush with (e.g., not protruding from) an outer surface 404 of the belt 310 along portions of the belt 310 that are passing along a relatively straight line, and to extend from the belt 310 as the belt 310 bends (e.g., around both the distal end drum 324 and the proximal end drum 328). For instance, the one or more teeth 340 may remain flush with the outer surface 404 as the section of the belt 310 containing the one or more teeth 340 passes through the elongated shaft 312 and/or is not in contact with the distal end drum 324, the proximal end drum 328, and/or a tensioner or guide pulley 344. In other words, while the portion of the belt 310 containing the one or more teeth 340 is positioned in the elongated shaft 312, the portion of the belt 310 is substantially straight (e.g., the portion of the belt 310 does not exhibit much if any curvature) such that the one or more teeth 340 do not protrude from the surface of the portion of the belt 310. However, the one or more teeth 340 project beyond (e.g., protrude from) the outer surface 404 of the belt 310 along portions of the belt 310 that exhibit curvature. These portions of the belt 310 include portions where the belt 310 bends around the distal end drum 324 and/or the proximal end drum 328.

As can be seen in FIG. 4B, a tooth of the one or more teeth 340 may be at a location 408A. The tooth, while at location 408A, may be substantially flat or flush with the outer surface 404 of the belt 310. A different tooth of the one or more teeth 340 may be at a location 408B. While at the location 408B, due to the curvature of the belt 310, the tooth may project from the outer surface 404 of the belt 310. The tooth at location 408B is configured to cut anatomical tissue. In some embodiments, the one or more teeth 340 may be positionally offset from one another. For instance, the one or more teeth 340 may be offset (whether in alternating fashion or otherwise) from a centerline 412 running along a circumferential center of the belt 310. In such embodiments, the offset of the one or more teeth 340 may allow the one or more teeth 340 to be positioned relatively closer to one another and/or to provide a greater surface area of the belt 310 that is configured to cut anatomical tissue (e.g., so as to enable more efficient cutting of anatomical tissue).

The one or more teeth 340 may be configured to cut anatomical tissue when projecting beyond the surface of the belt 310. For instance, the tooth of the one or more teeth 340 at location 408B may project beyond the surface of the belt 310 and, when the distal end 308 of the cutting and cleaning tool 136 is positioned within a patient, contact anatomical tissue. The movement of the tooth relative to the anatomical tissue may cause the tooth to cut through the tissue. In some embodiments, the cutting motion of the tooth may cause the anatomical tissue to remain between the tooth at location 408B and the outer surface of the belt 310. In such embodiments, the portion of the belt 310 containing the tooth may move along the surface of the distal end drum 324 and then straighten, such that the tooth of the one or more teeth 340 becomes flush with the belt 310. The cut anatomical tissue may remain between the tooth and the belt 310. In other words, the tooth of the one or more teeth 340 may grasp the anatomical tissue between the tooth and the surface of the belt 310. In some embodiments, the cut anatomical tissue may remain between the tooth and the belt 310 until the portion of the belt 310 containing the tooth of the one or more teeth 340 passes around the proximal end drum 328. As the portion of the belt 310 containing the tooth of the one or more teeth 340 passes around the proximal end drum 328, the tooth of the one or more teeth 340 may bend so as to no longer be flush with the outer surface of the belt 310, and the anatomical tissue may no longer be pinned between the tooth of the one or more teeth 340 and the belt 310. In some embodiments, the anatomical tissue may be subject to one or more forces (e.g., centrifugal force from the rotational movement of the proximal end drum 328, gravity, combinations thereof, and/or the like) that may facilitate removal of the anatomical tissue from the tooth and/or belt 310.

In some embodiments, an irrigation system 208 and/or suction system 212 and components thereof (e.g., a suction conduit 332 and/or an irrigation conduit 336) may assist in removal of the anatomical tissue. For instance, the irrigation system 208 and/or the irrigation conduit 336 may provide a fluid spray (e.g., water) against the tooth of the one or more teeth 340 to detach or dislodge the anatomical tissue and/or any residue thereof from the tooth of the one or more teeth 340 and/or the belt 310. Similarly, the suction system 212 and/or the suction conduit 332 may provide a vacuum, resulting in a suction force on the anatomical tissue. After the anatomical tissue is removed from the belt 310, the anatomical tissue (as well as water provided by the irrigation conduit 336) may be removed from the housing 304 by the suction conduit 332.

In embodiments of the present disclosure where the one or more teeth 340 is defined by cuts in the belt 310, the transition from the one or more teeth 340 being flush with an outer surface 404 of the belt 310 to the one or more teeth 340 protruding from the outer surface 404 of the belt 310, and vice versa, occurs naturally due to the natural stiffness (e.g., resistance to bending) of the material from which the belt 310 is manufactured. This behavior beneficially aids in the cutting and removal of anatomical tissue from a patient, as the one or more teeth 340 are only operable to cut anatomical tissue when protruding from the outer surface 404 of the belt 310. Thus, the one or more teeth 340 will only cut anatomical tissue while passing around the distal end drum 324. This enables targeted cutting of anatomical tissue by the cutting and cleaning tool 136. Moreover, the one or more teeth 340 are configured to return to a flush position as the belt 310 straightens after passing around the distal end drum 324. As this occurs, anatomical tissue may beneficially be gripped between the one or more teeth 340 and the belt 310, and thus carried by the belt 310 through the elongated shaft 312 and back to the housing 304.

At the housing 304, the belt 310 is once again forced to bend as it passes around the proximal end drum 328. As this occurs, the one or more teeth 340 again protrude from the outer surface 404 of the belt 310, releasing any anatomical tissue that was previously being gripped between the one or more teeth 340 and the belt 310. In embodiments of the cutting and cleaning tool 136 that include or utilize a fluid system 208, fluid may also be sprayed onto the belt 310 to dislodge anatomical tissue therefrom and facilitate the collection and removal thereof from the housing 304 (e.g., using a suction system 212). Thus, embodiments of the present disclosure beneficially allow for targeted cutting of anatomical tissue, efficient removal of cut anatomical tissue from the subject, and efficient cleaning of the belt 310 and the one or more teeth 340 provided thereon, all while the cutting and cleaning tool 136 remains positioned with the distal end 308 inside the patient (e.g., without requiring repeated removal and reinsertion of the cutting and cleaning tool into the patient, whether for cleaning or otherwise).

The foregoing is not intended to limit the disclosure to the form or forms disclosed herein. In the foregoing Detailed Description, for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configuration. Thus, the following claims are hereby incorporated into this Detailed Description, with each claim standing on its own as a separate preferred embodiment of the disclosure.

Moreover, though the description has included description of one or more aspects, embodiments, and/or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A tool for cleaning a vertebral disc, the tool comprising:
   an elongated hollow shaft comprising a proximal end and a distal end;
   a first drum rotatably disposed in a housing secured to the proximal end of the hollow shaft, the first drum having a first axis;
   a second drum rotatably disposed proximate the distal end of the hollow shaft, the second drum having a second axis parallel to the first axis; and
   a belt that extends through the hollow shaft and is operatively coupled to the first drum and the second drum, the belt comprising a plurality of teeth configured to cut anatomical tissue,
   wherein each tooth of the plurality of teeth remains flush with an outer surface of the belt when a section of the belt comprising the tooth is substantially straight, and projects beyond the outer surface when the section of the belt bends around the first drum or the second drum.

2. The tool of claim 1, wherein the first drum is configured to drive the belt, wherein the second drum is freely rotatable, and wherein the belt extends at least partially around an outer circumferential surface of the second drum.

3. The tool of claim 1, wherein the plurality of teeth are formed from a plurality of C-shape cuts in the belt, and wherein the belt extends from a proximal end of the tool to a distal end of the tool.

4. The tool of claim 1, wherein the plurality of teeth are offset to alternating sides of the belt.

5. The tool of claim 1, wherein the housing comprises an irrigation system and a suction system.

6. The tool of claim 5, wherein at least one of the irrigation system and the suction system is disposed proximate to the second drum.

7. The tool of claim 1, wherein at least one portion of the belt is made from stainless steel.

8. The tool of claim 1, further comprising:
   a motor, the motor configured to drive at least one of the first drum and the second drum.

9. The tool of claim 1, wherein each tooth of the plurality of teeth is configured to grasp anatomical tissue between the tooth and the outer surface of the belt when a portion of the belt comprising the tooth is substantially straight, and release the anatomical tissue when the section of the belt comprising the tooth bends around an outer circumferential surface of the second drum.

10. A device for cleaning a vertebral disc, the device comprising:
    a housing;
    a first rotatable cylinder disposed in a first axial orientation within and proximate a proximal end of the housing;
    a second rotatable cylinder disposed outside a distal end of the housing in the first axial orientation; and
    a belt that extends between the first rotatable cylinder and the second rotatable cylinder, extends at least partially around an outer circumferential surface of the second rotatable cylinder, and is operatively coupled to the first rotatable cylinder and the second rotatable cylinder, the belt comprising a plurality of cutting tabs, wherein each cutting tab of the plurality of cutting tabs remains flush with an outer surface of the belt when a section of the belt comprising the cutting tab is substantially straight, and projects beyond the outer surface when the section of the belt bends around the first rotatable cylinder or the second rotatable cylinder.

11. The device of claim 10, wherein the belt is a chain.

12. The device of claim 10, wherein the plurality of cutting tabs are formed from a plurality of C-shape cuts in the belt.

13. The device of claim 10, wherein the housing comprises a hollow shaft extending at least partially from the distal end toward the proximal end.

14. The device of claim 13, further comprising an irrigation system and a suction system, wherein the irrigation system comprises a fluid conduit configured to dispense a fluid onto at least one surface of the belt within the housing.

15. The device of claim 14, wherein the fluid conduit dispenses the fluid radially from within the first rotatable cylinder.

16. The device of claim 14, wherein the suction system comprises a conduit configured to remove anatomical tissue from the housing.

17. The device of claim 10, wherein the first rotatable cylinder has a larger diameter than the second rotatable cylinder.

18. The device of claim 10, wherein the plurality of cutting tabs are formed from a plurality of triangle-shape cuts in the belt.

19. A system for removing anatomical tissue from a vertebral disc, the system comprising:
   a cutting device comprising:
      an elongated hollow shaft comprising a proximal end and a distal end;
      a first drum rotatably disposed in a housing secured to the proximal end of the hollow shaft, the first drum having a first axis;
      a second drum rotatably disposed proximate the distal end of the hollow shaft, the second drum having a second axis parallel to the first axis; and
      a belt that extends through the hollow shaft, extends at least partially around an outer circumferential surface of the second drum, and is operatively coupled to the first drum and the second drum, the belt comprising a plurality of cleaning teeth configured to cut anatomical tissue, wherein each tooth of the plurality of cleaning teeth remains flush with an outer surface of the belt when a section of the belt comprising the tooth is substantially straight, and projects beyond the outer surface when the section of the belt bends around the first drum or the second drum;
   a drive system operably connected to the first drum and configured to rotate the first drum about the first axis;
   a fluid system configured to dispense a fluid into the housing; and
   a suction system configured to remove the fluid and anatomical tissue from within the housing.

20. The system of claim 19, wherein the plurality of cleaning teeth are formed from a plurality of C-shape cuts in the belt.

* * * * *